United States Patent
Gilad et al.

(10) Patent No.: US 9,339,174 B2
(45) Date of Patent: May 17, 2016

(54) DEVICE AND METHOD FOR VIEWING A BODY LUMEN

(75) Inventors: Zvika Gilad, Haifa (IL); Amit Pascal, Haifa (IL)

(73) Assignee: GIVEN IMAGING LTD, Yoqneam (IL)

( * ) Notice: Subject to any disclaimer, the term of this patent is extended or adjusted under 35 U.S.C. 154(b) by 1223 days.

(21) Appl. No.: 12/174,779

(22) Filed: Jul. 17, 2008

(65) Prior Publication Data

US 2009/0023992 A1 Jan. 22, 2009

Related U.S. Application Data

(60) Provisional application No. 60/929,923, filed on Jul. 18, 2007.

(51) Int. Cl.
- *A61B 1/00* (2006.01)
- *A61B 1/06* (2006.01)
- *A61B 1/04* (2006.01)
- *A61B 1/05* (2006.01)

(52) U.S. Cl.
CPC . *A61B 1/04* (2013.01); *A61B 1/041* (2013.01); *A61B 1/00101* (2013.01); *A61B 1/00183* (2013.01); *A61B 1/053* (2013.01)

(58) Field of Classification Search
CPC ............ A61B 1/0125; A61B 1/00174; A61B 1/00177; A61B 1/00179; A61B 1/00181; A61B 1/00183
USPC .................. 600/109, 113–114, 160, 172–173
See application file for complete search history.

(56) References Cited

U.S. PATENT DOCUMENTS

| | | | |
|---|---|---|---|
| 4,198,960 | A | 4/1980 | Utsugi |
| 4,278,077 | A | 7/1981 | Mizumoto |
| 4,782,819 | A | 11/1988 | Adair |
| 4,819,620 | A | 4/1989 | Okutsu |
| 4,905,670 | A | 3/1990 | Adair |
| 5,026,368 | A | 6/1991 | Adair |
| 5,143,054 | A | 9/1992 | Adair |
| 5,381,784 | A | 1/1995 | Adair |
| 5,604,531 | A | 2/1997 | Iddan et al. |

(Continued)

FOREIGN PATENT DOCUMENTS

| | | |
|---|---|---|
| JP | 3-159629 | 7/1991 |
| JP | 05-068666 | 3/1993 |

(Continued)

OTHER PUBLICATIONS

L. Aabakken et al. Capsule Endoscopy in a Patient With Zenker's Diverticulum Endoscopy 2003; 35:799.*

(Continued)

*Primary Examiner* — John P Leubecker
*Assistant Examiner* — Arnaldo Torres Diaz
(74) *Attorney, Agent, or Firm* — Pearl Cohen Zedek Latzer Baratz LLP

(57) ABSTRACT

A device and method for viewing a body lumen are provided. An assembly of a capsule endoscope and an endoscope is inserted into a body lumen. The capsule endoscope is positioned within the body lumen at a predetermined distance from the endoscope, and images are obtained from opposite sides of a desired location in the body lumen. In vivo procedures may be performed, while images of the procedure are obtained from opposite sides of the procedure location.

23 Claims, 8 Drawing Sheets

(56) References Cited

U.S. PATENT DOCUMENTS

| | | | |
|---|---|---|---|
| 5,653,677 A * | 8/1997 | Okada et al. | 600/112 |
| 5,667,473 A * | 9/1997 | Finn et al. | 600/104 |
| 6,240,312 B1 | 5/2001 | Alfano et al. | |
| 6,689,056 B1 * | 2/2004 | Kilcoyne et al. | 600/300 |
| 6,986,738 B2 | 1/2006 | Glukhovsky et al. | |
| 7,009,634 B2 | 3/2006 | Iddan et al. | |
| 7,578,788 B2 * | 8/2009 | Yokoi et al. | 600/160 |
| 2002/0007111 A1 * | 1/2002 | Deckert et al. | 600/177 |
| 2002/0103417 A1 | 8/2002 | Gazdzinski | |
| 2002/0109774 A1 | 8/2002 | Meron et al. | |
| 2002/0128539 A1 * | 9/2002 | Higuma et al. | 600/133 |
| 2002/0165444 A1 * | 11/2002 | Whitman | 600/407 |
| 2003/0013938 A1 * | 1/2003 | Iddan et al. | 600/129 |
| 2003/0120130 A1 * | 6/2003 | Glukhovsky et al. | 600/109 |
| 2003/0139647 A1 * | 7/2003 | Raz et al. | 600/104 |
| 2003/0153866 A1 * | 8/2003 | Long et al. | 604/28 |
| 2004/0133076 A1 * | 7/2004 | Kobayashi et al. | 600/175 |
| 2004/0267095 A1 * | 12/2004 | Miyake et al. | 600/175 |
| 2005/0085697 A1 * | 4/2005 | Yokoi et al. | 600/160 |
| 2005/0165272 A1 * | 7/2005 | Okada et al. | 600/114 |
| 2005/0256372 A1 * | 11/2005 | Yokoi et al. | 600/102 |
| 2007/0015961 A1 | 1/2007 | Yamamoto et al. | |
| 2007/0049796 A1 | 3/2007 | Fujikura | |
| 2007/0161855 A1 * | 7/2007 | Mikkaichi et al. | 600/113 |
| 2007/0161862 A1 * | 7/2007 | Yokoi et al. | 600/175 |
| 2007/0173691 A1 * | 7/2007 | Yokoi et al. | 600/118 |
| 2007/0255099 A1 * | 11/2007 | Yokoi et al. | 600/109 |
| 2007/0255100 A1 * | 11/2007 | Barlow et al. | 600/114 |
| 2008/0015413 A1 * | 1/2008 | Barlow et al. | 600/114 |
| 2008/0027283 A1 * | 1/2008 | Matsui et al. | 600/127 |
| 2008/0117291 A1 * | 5/2008 | Hirakawa et al. | 348/65 |
| 2008/0154093 A1 * | 6/2008 | Cho et al. | 600/114 |
| 2008/0167523 A1 * | 7/2008 | Uchiyama et al. | 600/114 |
| 2008/0275298 A1 * | 11/2008 | Ratnakar | 600/109 |
| 2009/0018396 A1 * | 1/2009 | Takizawa et al. | 600/127 |
| 2009/0306470 A1 * | 12/2009 | Karasawa et al. | 600/103 |
| 2010/0198009 A1 * | 8/2010 | Farr et al. | 600/109 |
| 2011/0208011 A1 * | 8/2011 | Ben-Horin | 600/300 |

FOREIGN PATENT DOCUMENTS

| | | |
|---|---|---|
| JP | 2000-342527 | 12/2000 |
| JP | 2006-141725 | 6/2006 |
| JP | 2006141725 A * | 6/2006 |
| JP | 2007-125356 | 5/2007 |
| JP | 2008-067909 | 3/2008 |
| WO | WO 01/65995 | 9/2001 |
| WO | WO 2005104927 | 11/2005 |

OTHER PUBLICATIONS

Office Action for Japanese Application No. 2007-187158 mailed Jun. 5, 2012.

* cited by examiner

DEVICE AND METHOD FOR VIEWING A BODY LUMEN

CROSS-REFERENCE TO RELATED APPLICATIONS

This application claims the benefit of U.S. Provisional Patent Application No. 60/929,923, filed on Jul. 18, 2007, which is incorporated in its entirety herein by reference.

FIELD OF THE INVENTION

The present invention relates to the field of in vivo viewing. More specifically, the present invention relates to an in vivo device and methods for viewing a body lumen through either an endoscope or a capsule endoscope, or through both.

BACKGROUND OF THE INVENTION

Medical procedures in body lumens and cavities, such as gastroenterology procedures and laparoscopic surgery procedures, may require specifically designed medical devices. Typically, the devices include a performing end (distal end) functionally coupled to a controlling end (proximal end). The performing end, which is inserted into the body, is operated and manipulated by the controlling end, which is accessible to an external operator.

In some cases the device further includes a viewing or imaging element for simultaneously viewing and performing a procedure in vivo. In that case the device may be connected to a cable that connects the viewing or imaging element to an external power supply system, a light source and a processing unit.

A common device for in-vivo procedures, which includes an imager, is the endoscope. Endoscopes typically comprise a tube, which is inserted into the body, comprising channels that are utilized for air insertion, water injection, suction, viewing or imaging, and for passing medical devices through them into the body. The tube is connected, at its proximal end, to a control body that is held by an external operator.

Capsule endoscopes are also known devices used for viewing or imaging in vivo.

Capsule endoscopes may comprise an imager, at least one illumination source, and an optical system. Capsule endoscopes may also comprise other sensors which may sense the in vivo environment, such as temperature sensors, pH sensors, pressure sensors etc.

Capsule endoscopes may be either autonomous, whereby they comprise an internal power supply, such as a battery, or they may be wired to an external power supply.

Capsule endoscopes may be in any shape suitable to be inserted inside the body lumen, e.g., sphere, ellipsoid, etc.

The angle of view afforded by an imager or the accessibility of such a sensor that is located at the endoscope tip, or behind the optical window of the capsule, to remote or concealed portions of the body lumen, such as the colon in the gastrointestinal (GI) tract, which also has many folds inside, is limited.

More so, when performing a procedure in vivo, it is usually necessary to view all that is being performed in real-time. In an area which includes many folds, e.g. the colon, the endoscope's imager may not be able to view a pathology placed within a fold, which limits the caregiver from viewing what he is performing at all times and from all angles.

SUMMARY OF THE INVENTION

Embodiments of the present invention provide a device and methods for better viewing and/or imaging a body lumen.

In some embodiments of the invention, the in vivo imaging device used for viewing may be autonomous. In some embodiments, for example, the in vivo imaging device may include a swallowable capsule endoscope. According to some embodiments, the in-vivo imaging device comprises at least one imager, at least one illumination source and an optical system. In some embodiments, the imaging device's housing may comprise a curved portion so as to conform to a contour of a second in vivo device.

In some embodiments the imaging device may have a shape configured for fully or partially wrapping the outer surface of a second device, e.g. an endoscope, colonoscope, Double-Balloon Endoscopy™ system, catheter, needle, laparoscope etc. In some embodiments, the shape of the imaging device's housing may be designed to have a curve which may fit an outer section of different devices having a spherical, square or other shaped profile. In some embodiments, the in vivo imaging device may be connected to an endoscope type device. According to some embodiments, the imaging device is connected to the endoscope through at least two semi rigid cables of a predetermined length. Typically, the number of connectors between the capsule and the endoscope is at least two, for easier and more stabilized positioning of the capsule in relation to the endoscope.

A method for viewing a body lumen, according to one embodiment of the invention, comprises inserting into the body lumen an assembly of a capsule endoscope and an endoscope. Following insertion of both the capsule and endoscope, the capsule is positioned within the body lumen at a predetermined distance from the endoscope, and images can be obtained from opposite sides of a desired location in the body lumen using the capsule and endoscope's imaging units. According to some embodiments, the method may include performing an in vivo procedure at the desired location, while obtaining images from opposite sides of the location of the procedure. According to some embodiments, the capsule endoscope comprises at least one imager, at least one illumination source and an optical system. In some embodiments, the imager, illumination source and optical system of the capsule endoscope, are positioned behind an optical window. In some embodiments, the capsule endoscope comprises two optical windows, typically positioned on opposite sides of the capsule.

In some embodiments, the capsule endoscope is connected to the endoscope.

According to some embodiments of the invention, the capsule endoscope is connected to the endoscope, for example, through at least two semi rigid cables of a predetermined length, while the cables are positioned on the outer surface of the endoscope. According to some embodiments, at the time of insertion of the capsule endoscope into the body lumen, the capsule is partially wrapped about the outer surface of the endoscope.

According to some embodiments, the capsule endoscope comprises a transmitter.

The transmitter may be a wireless transmitter or may be wired to the endoscope's power supply. In some embodiments, the capsule power supply is external, and power is passed through an electrical wire connected to the endoscope. In some embodiments, the capsule endoscope comprises a receiver, for example, for receiving control signals from an external transceiver.

A method for viewing a body lumen, according to another embodiment of the invention, comprises inserting into a body lumen a capsule endoscope and an endoscope, followed by guiding the endoscope to a desired location in the body lumen, using images obtained by the capsule endoscope. In some embodiments, the method includes performing an in vivo procedure at the desired location while obtaining images from opposite sides of said procedure, using both the capsule and the endoscope. In some embodiments, the capsule endoscope comprises at least one imager, at least one illumination source and an optical system. In some embodiments, the capsule endoscope comprises two optical windows, typically positioned on opposite sides of the capsule.

A method for viewing a body lumen, according to yet another embodiment, comprises inserting into a body lumen a capsule endoscope and an endoscope, followed by guiding the endoscope in the body lumen, using images obtained by the capsule endoscope, until no further movement of the endoscope is possible. After the endoscope has reached the farthest area it can inside the body lumen, the capsule endoscope is lead further or let free to be passively moved further in the body lumen, without the endoscope, while still being attached to the endoscope, and then images of the body lumen are obtained using the capsule endoscope. According to some embodiments, the capsule endoscope may be able to perform an in vivo procedure on its own, such as those an endoscope performs, e.g. stitching to close perforation, taking a biopsy, removing polyps, and other suitable procedures and treatment enabled by an endoscope. In some embodiments, the capsule endoscope may have an ability to sense the in vivo environment surrounding it, e.g. sense temperature, pressure, pH, conductivity, etc.

A method for viewing a body lumen, according to yet another embodiment of the invention, comprises inserting into a body lumen a capsule endoscope, immobilizing the capsule at a desired location in the body lumen, inserting into the body lumen an endoscope to the desired location in which the capsule is immobilized at, and obtaining images from different (such as opposite) sides of that desired location, using both the capsule and the endoscope's imaging units.

BRIEF DESCRIPTION OF THE DRAWINGS

The present invention will be understood and appreciated more fully from the following detailed description taken in conjunction with the appended drawings in which.

DETAILED DESCRIPTION OF THE INVENTION

Figure 1A:
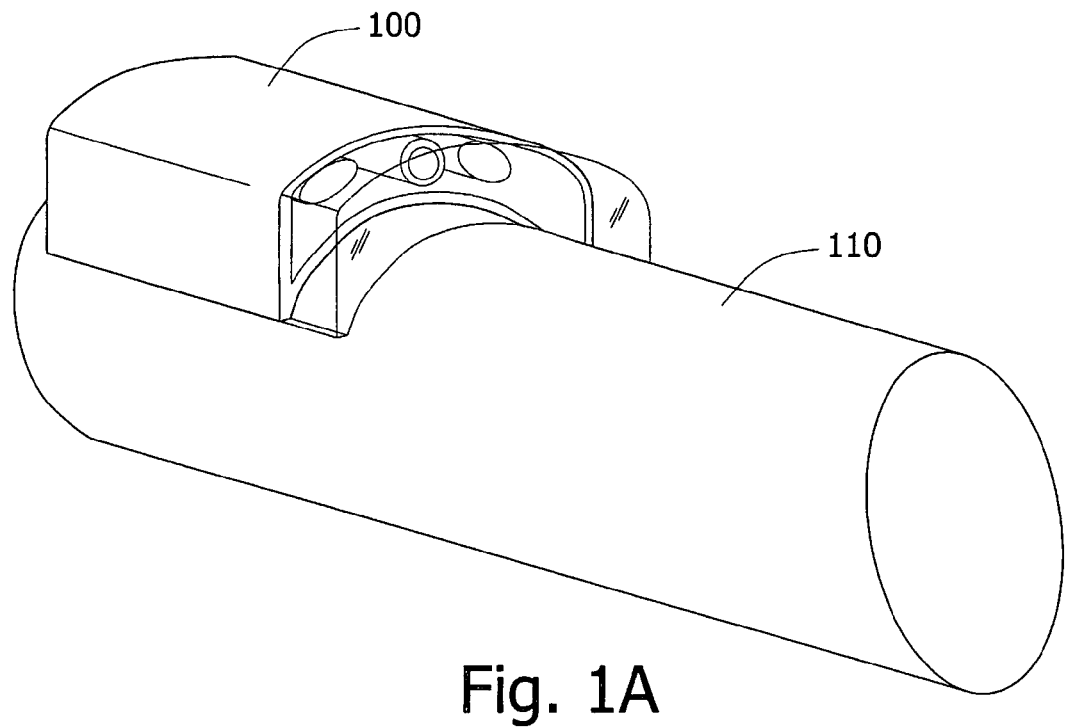
FIGS. 1A-1B are a schematic illustration of an in vivo assembly in accordance with one embodiment of the invention.

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as to not obscure the present invention.

Some embodiments of the present invention are directed to a typically swallowable in-vivo device. Some embodiments are directed to a capsule endoscope connected to an endoscope that may actively progress through a body lumen, e.g., the gastro-intestinal (GI) tract. In some embodiments, the in vivo imaging device may include in addition to an imaging unit or an imager, other sensors, for example, a pH sensor, a temperature sensor, a pressure sensor, sensors of other in-vivo parameters, or the like. Devices systems and methods according to some embodiments of the present invention, may be similar to embodiments described in U.S. Pat. No. 7,009,634 to Iddan et al., entitled "A Device and System for In-Vivo Imaging", and/or in U.S. patent application Ser. No. 10/046, 541, entitled "System and Method for Wide Field Imaging of Body Lumens", filed on Jan. 16, 2002, published on Aug. 15, 2002 as United States Patent Application Publication Number 2002/0109774, each of which are assigned to the common assignee of the present invention and each of which are hereby incorporated by reference in their entirely. Devices and systems as described herein may have other configurations and/or sets of components. For example, an external receiver/recorder unit, a processor and a monitor, e.g., in a workstation, such as those described in the above publications, may be suitable for use with some embodiments of the present invention. Some in vivo imaging devices may be capsule shaped, or may have other shapes, for example, a peanut shape or tubular, spherical, conical, or other suitable shapes. Some embodiments of the present invention may include, for example, a typically swallowable capsule endoscope. In other embodiments, an in vivo imaging device need not be swallowable and/or autonomous, and may have other shapes or configurations. Some embodiments of the present invention may include an endoscope which is externally maneuvered. In some embodiments an endoscope may be a gastroscope inserted through the mouth of a patient or may be a colonoscope inserted through the anus of a patient. In some embodiments, the endoscope may be a Double-Balloon Endoscopy™ system by FUJINON, or a similar device, inserted from either direction decided on by the physician; from the mouth so as to reach the small bowel from the top, or from the anus to the colon so as to view the end of the small bowel.

Embodiments of the capsule endoscope are typically autonomous and are typically self-contained. For example, all of the capsule endoscope's components are substantially contained within a container, housing or shell, and the capsule does not require any wires or cables to, for example, receive power or transmit information. The capsule may communicate with an external receiving and display system to provide display of data, control, or other functions. For example, power is provided by an internal battery or an internal power source, or using a wired or wireless power-receiving system. Other embodiments may have other configurations and capabilities. For example, components may be distributed over multiple sites or units; and control information or other information may be received from an external source.

Figure 1B:
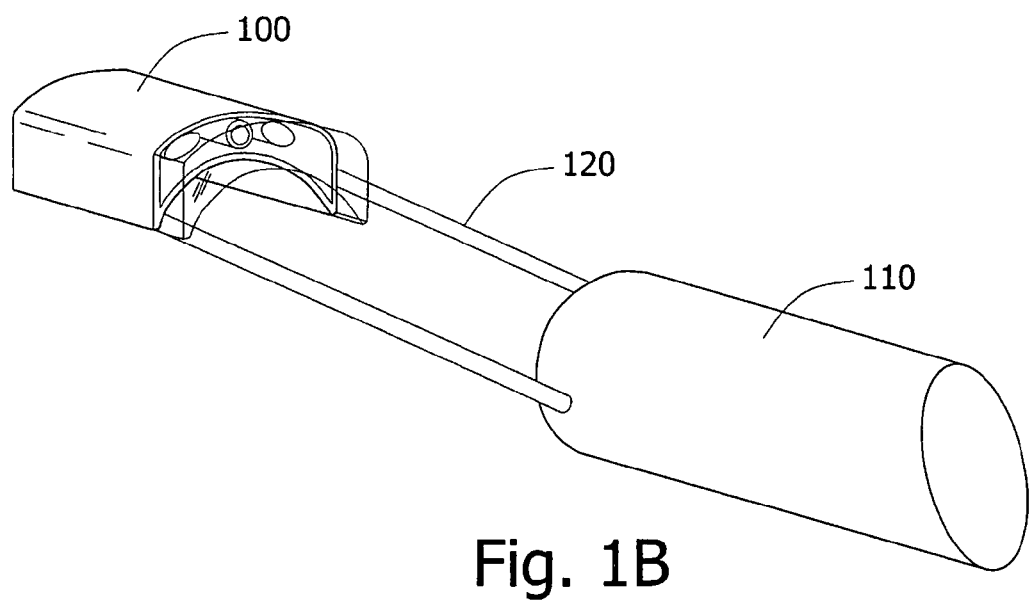

Reference is now made to FIGS. 1A-1D. FIGS. 1A-1B schematically illustrate an in vivo assembly in accordance with one embodiment of the invention. FIG. 1A illustrates an in vivo imaging device 100 partially wrapped about the outer surface of an endoscope 110. This preferred imaging device 100 and endoscope 110 embodiment helps keep a minimum diameter size of the imaging device 100 and endoscope 110 assembly at the time of insertion into a body lumen, while not blocking the field of view of endoscope 110 (as may have been if the imaging device 100 was in continuation to endoscope 110).

This imaging device 100 and endoscope 110 assembly may be inserted into a body lumen for viewing and/or obtaining images of it. In some embodiments, an in vivo procedure is performed at a desired location in the body lumen, while viewing and/or imaging the location. In some embodiments, imaging device 100 may be connected to endoscope 110 through detachable means, such as non-permanent glue, clips, snaps etc.

This will enable detachment of imaging device 100 from endoscope 110 at a desired point in time, for example, the end of the procedure. According to some embodiments, imaging device 100 may be situated on other devices besides an endoscope, e.g., colonoscope, Double-Balloon Endoscopy™ system, catheter, needle, laparoscope etc. In some embodiments, the imaging device may also be placed on a physician's finger. In some embodiments imaging device 100 is autonomous and comprises an internal power source. According to some embodiments device 100 can be replaced before each insertion into a body lumen.

In some embodiments, imaging device 100 may be wired to an external power supply, e.g., endoscope 110 power supply. FIG. 1B illustrates another embodiment of an in vivo assembly in which imaging device 100 is connected to endoscope 110 through at least two semi rigid cables 120. In some embodiments the length of cables 120 is predetermined. Typically, the predetermined length of cables 120 connecting imaging device 100 to endoscope 110 may be determined by the optical systems' conditions in both imaging device 100 and endoscope 10. The predetermined length should preferably ensure a good and focused view and/or images of the body lumen at all times. In other embodiments, the distance between imaging device 100 and endoscope 110 is not limited. In some embodiments, cables 120 are positioned on the outer surface of endoscope 10; however cables 120 may be positioned anywhere suitable. Following insertion of this imaging device 100 and endoscope 110 assembly, as shown in FIG. 1A, into a body lumen, imaging device 100 may be pushed forward using, for example, the semi rigid cables, so as to be placed at a distance from endoscope 110. This configuration is useful when there is a need for obtaining images of a desired location in the body lumen from different sides to have a wider field of view of the desired location, e.g., when performing an in vivo procedure. In some embodiments, as shown in FIGS. 1A-1B, endoscope 110 is looking forward, (for example, the forward direction of movement) while imaging device 100 is looking backwards. After imaging device 100 is pushed forward to a distance from endoscope 110 as shown in FIG. 1B, the imaging device 100 and endoscope 110 are looking at the same desired location in the body lumen, typically from opposite sides. In some embodiments, the imaging device 100 may comprise two optical windows positioned on opposite sides of the device.

Figure 1C:
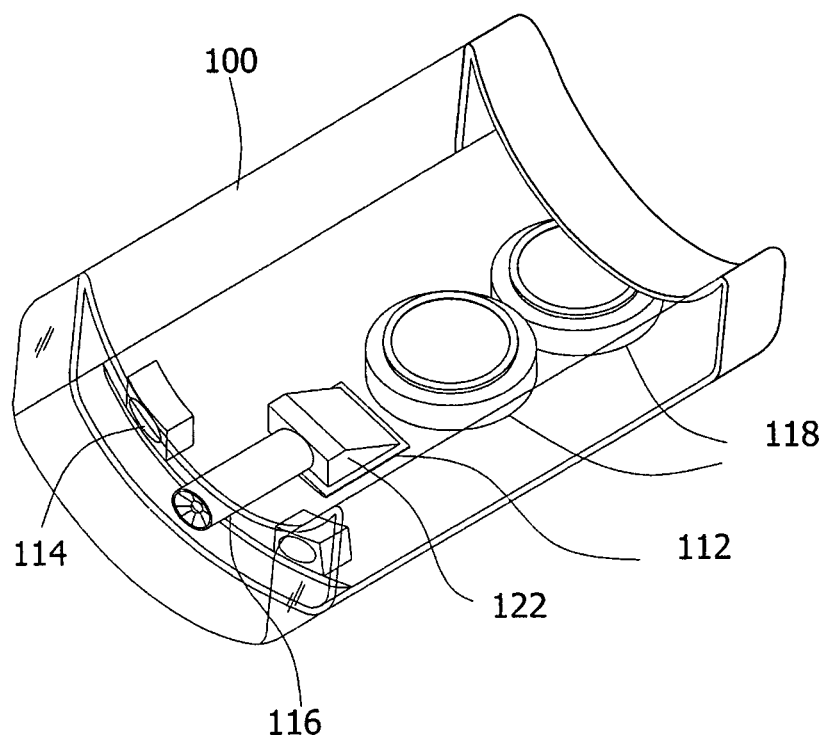
FIGS. 1C-1D are a schematic illustration of an in vivo imaging device in accordance with one embodiment of the invention.
Figure 1D:
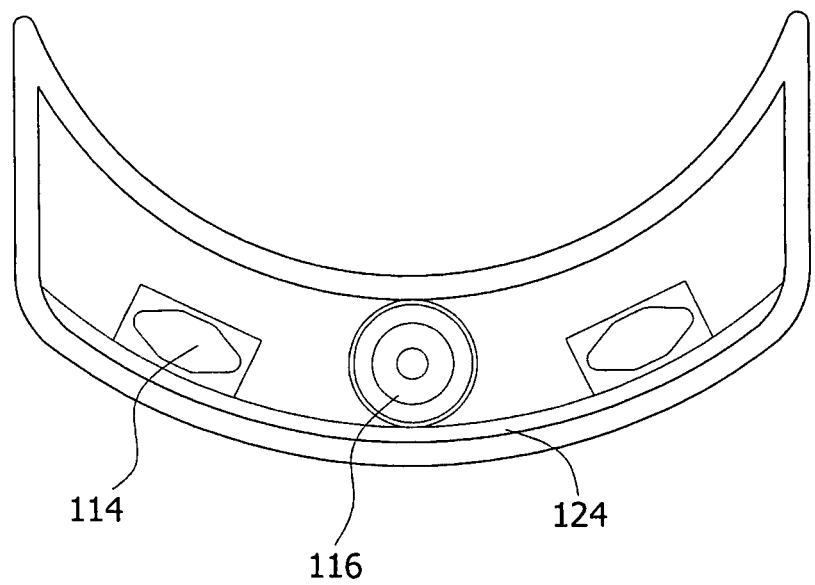

FIGS. 1C-1D schematically illustrate an in vivo imaging device in accordance with one embodiment of the invention. FIG. 1C illustrates imaging device 100 comprising at least one imager 112, at least one illumination source 114 an optical system 116, and an internal power source, e.g., at least one battery 118. In some embodiments, all of imaging device's 100 components are positioned behind an optical window. In some embodiments the housing of imaging device 100 may have a concave shape.

According to some embodiments, the shape of the housing of imaging device 100 may be designed to have a curve which may fit the contour of different devices, e.g., endoscope, colonoscope, Double-Balloon Endoscopy™ system, catheter, needle, laparoscope etc. In some embodiments, imaging device 100 may have a shape configured for fully or partially surrounding the outer surface of another device having a spherical, square or any other shaped cross section. In some embodiments, lenses in optical system 116 may be positioned on top of imager 112 to focus light reflected from a body lumen onto the imager 112. In some embodiments, optical system 116 may comprise a prism 122 positioned above imager 112. In some embodiments, lenses in optical system 116 may not be placed over the imager, but there may be a prism 122 mounted on the imager 112.

In some embodiments, prism 122 focuses light reflected from a body lumen which then passes through the lenses, onto imager 112. In some embodiments, optical system 116 may comprise one or more mirrors, prisms, composite lenses or any other suitable focusing and/or light directing elements. In some embodiments, LEDs 114 may be placed around optical system 116. FIG. 1D illustrates a front view of imaging device 100. FIG. 1D illustrated the illumination source 114, optical system 16 and PCA 124 on which the electrical elements are situated. In some embodiments, PCA 124 may be flexible or may be designed to fit the contour of the housing of imaging device 100.

Figure 2A:
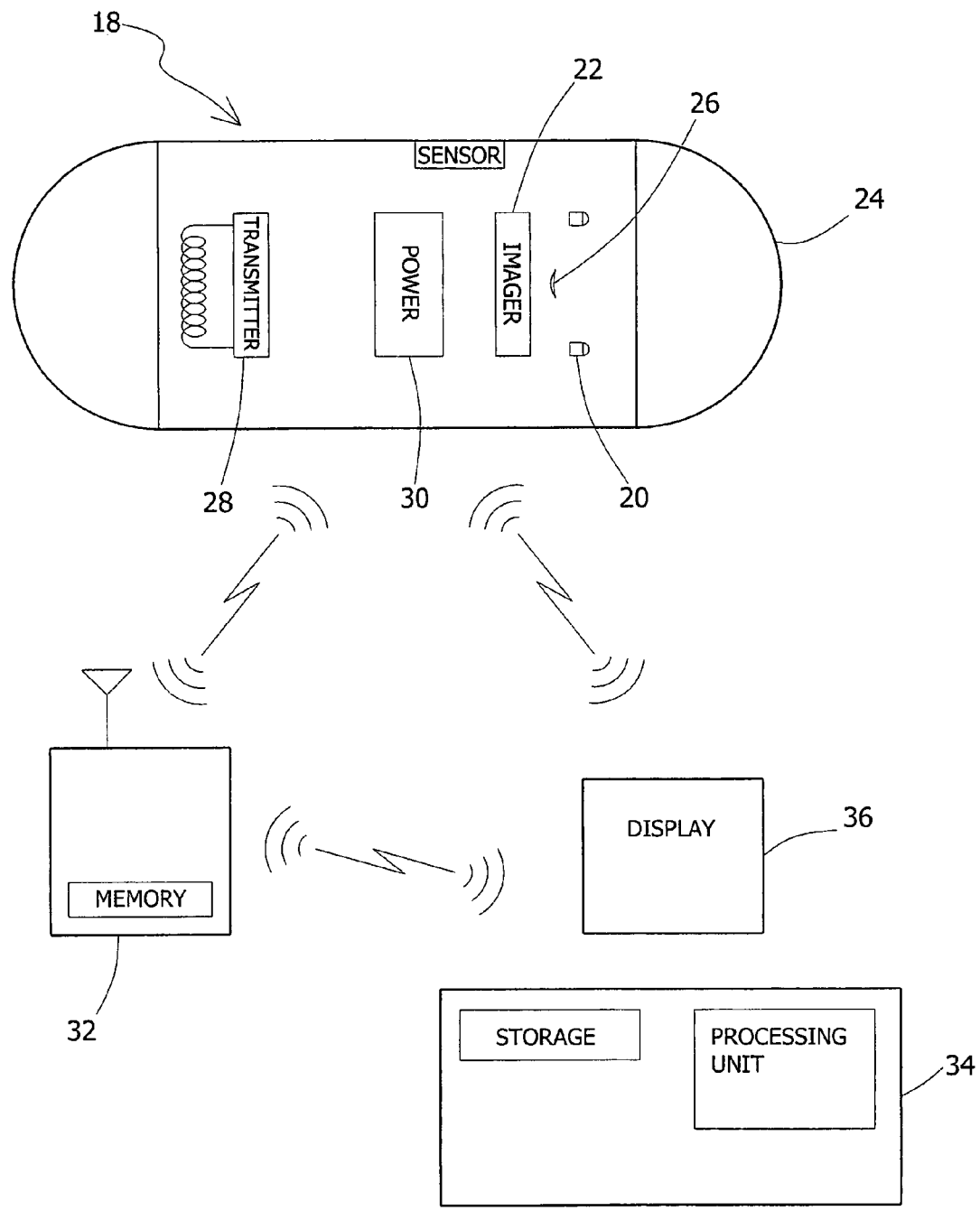
FIG. 2A is a schematic illustration of a system in accordance with one embodiment of the invention.

FIG. 2A schematically illustrates a system in accordance with one embodiment of the invention. FIG. 2A illustrates a capsule endoscope 18 comprising illumination sources 20, imager 22, power source 30, and optical system 26. In some embodiments, the illumination sources 20, imager 22, power source 30 and optical system 26 are positioned behind optical window 24. According to some embodiments, capsule endoscope 18 may comprise two optical windows, typically on opposite sides of capsule endoscope 18. Behind each of the two optical windows are positioned at least one imager, at least one illumination source and an optical system. Image (and other) data transmitted from the capsule through transmitter 28, may be received out side a patient's body by a receiver 32 placed on or near the patient's body. The data may then be transferred to a workstation 34, which comprises a storage unit and a processing unit for processing the data before or after storage. The data before or after processing, may be displayed on a display 36 of the workstation 34 for a physician to view during or after a procedure. In some embodiments, transmitter 28 may essentially include a wireless transmitter, e.g., able to operate using radio waves, able to transmit Radio Frequency (RF) signals, or able to transmit other types of communication signals. For example, transmitter 28 may transmit wireless signals utilizing an antenna. Other wireless methods of transmission may be used. In some embodiments, receiver 32 may be a wireless (e.g., RF) receiver, able to receive signals from an external transmitter. In some embodiments the receiver 32 and workstation 34 are integrated into one unit. In yet another embodiment, the receiver 32 and transmitter 28 may be bi-directional. Receiver 32 may receive data transmitted by the transmitter 28 and send command signals to the transmitter 28 e.g., to activate and/or otherwise control one or more components of capsule 18. In some embodiments, when the capsule endoscope 18 comprises an assembly with an endoscope, display 36 may be a combined display of both the capsule endoscope 18 and the endoscope.

Figure 2B:
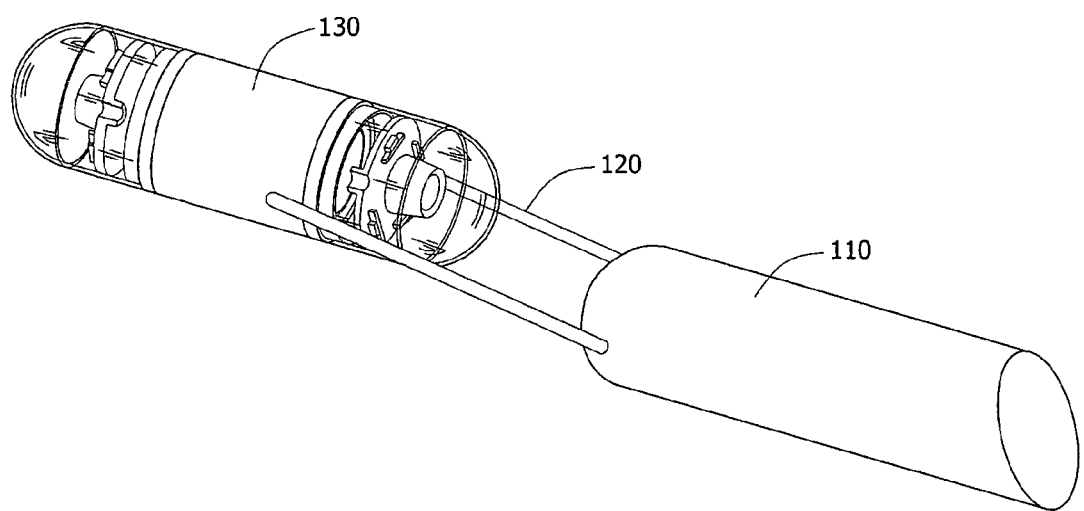
FIG. 2B is a schematic illustration of an in vivo assembly in accordance with one embodiment of the invention.

FIG. 2B schematically illustrates an in vivo assembly in accordance with one embodiment of the invention. FIG. 2B illustrates an assembly in which capsule endoscope 130, which comprises two optical windows, typically positioned on opposite sides of the capsule, is connected to endoscope 110 through at least two semi rigid cables 120. In some embodiments the length of cables 120 is predetermined. Typically, the predetermined length of cables 120 connecting capsule endoscope 130 to endoscope 110 may be determined by the optical systems' conditions in both capsule endoscope 130 and endoscope 110. The predetermined length should preferably ensure a good and focused view and/or images of the body lumen at all times. In other embodiments, the distance between capsule endoscope 130 and endoscope 110 is not limited. In some embodiments, cables 120 are positioned on the outer surface of endoscope 110; however cables 120 may be positioned anywhere suitable. Following insertion of capsule endoscope 130 and endoscope 110 assembly into a body lumen, capsule endoscope 130 may be pushed forward using, for example, the semi rigid cables, so as to be placed at a distance from endoscope 110. This configuration is useful when there is a need for obtaining images of a desired location in the body lumen from different sides to have a wider field of view of the desired location, e.g., when performing an in vivo procedure. In some embodiments, behind each of the two optical windows of capsule endoscope 130, are positioned at least one imager, at least one illumination source and an optical system. In some embodiments, endoscope 110 is looking forward, (for example, the forward direction of movement) while capsule endoscope 130 may be looking forward and backwards, using both optical windows. After capsule 130 is pushed forward to a distance from endoscope 110, the capsule 130 and endoscope 110 may look at the same desired location in the body lumen, typically from opposite sides. The capsule 130 may view the lumen through either one of its optical windows (or through both), typically through the optical window which looks at the opposite side of the side endoscope 110 views.

Figure 3:
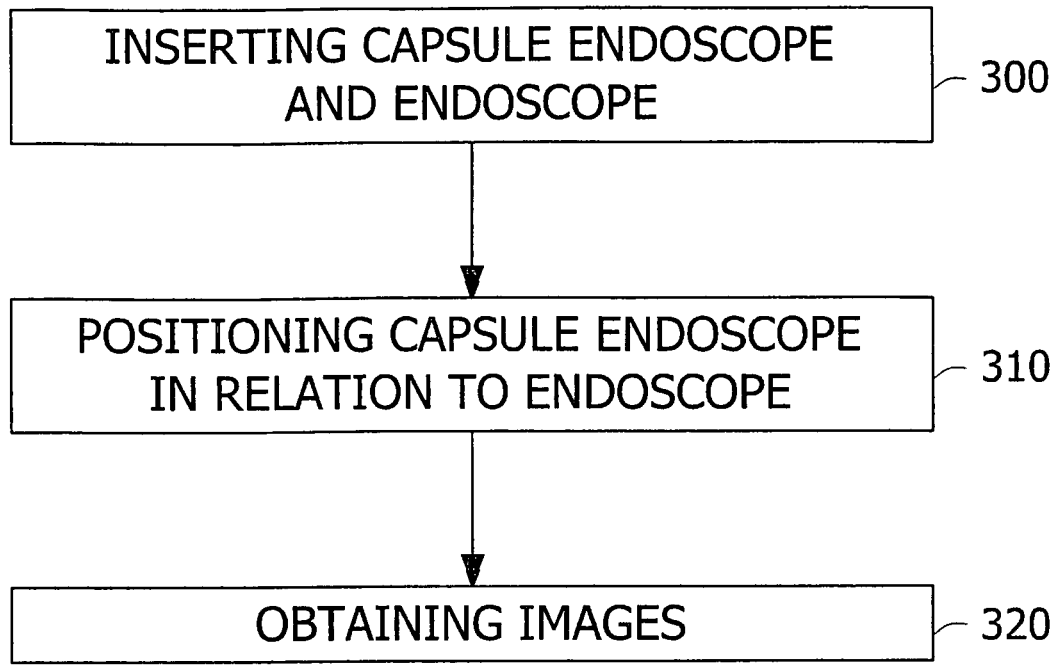
FIG. 3 depicts a method according to one embodiment of the present invention.

FIG. 3 depicts a method according to one embodiment of the present invention. Referring to FIG. 3, in step 300, a capsule endoscope and an endoscope assembly is inserted in vivo, into a body lumen. In some embodiments, the capsule endoscope and the endoscope are attached. According to one embodiment the capsule and endoscope are attached through at least two semi rigid cables of a predetermined length. Typically, the predetermined length of the cables connecting the capsule to the endoscope may be determined by the optical conditions in both the capsule and endoscope. The predetermined length should preferably ensure a good and focused view and/or images of the body lumen at all times. In some embodiments, the cables are positioned on the outer surface of the endoscope; however the cables may be positioned anywhere suitable.

According to other embodiments the capsule is attached to the endoscope by a single cable, wire or any other suitable attaching means. According to some embodiments the capsule need not be attached to the endoscope. In some embodiments of the present invention, the capsule endoscope may be partially wrapped about the outer surface of said endoscope when inserted into the body lumen with the endoscope. This preferred embodiment helps keep a minimum diameter size of the capsule endoscope and endoscope assembly at the time of insertion. In some embodiments, the capsule endoscope may be attached to the front part of the endoscope, which may or may not interfere with the endoscope's field of view. In step 310, the capsule endoscope is positioned in relation to the endoscope. The capsule is moved, for example, forward using the cables connecting the capsule to the endoscope, up to a pre-determined length of the cables. This positioning is typically maneuvered externally, or may be done automatically. In step 320, both the capsule endoscope and the endoscope obtain images using their imaging units. Preferably, the capsule and endoscope obtain images of opposite sides of the body lumen they are at. According to other embodiments other angles of viewing may be used.

In some embodiments, at the time of insertion, the imaging unit of the capsule is the only unit viewing and/or imaging the step of insertion. In other embodiments, the imager of the endoscope is the only device viewing and/or imaging, or the capsule and endoscope may both be able to view the step of inserting into the body lumen. In some embodiments, after the capsule is positioned at a pre-determined length from the endoscope, both devices obtain images of the body lumen that is positioned in between them. In some embodiments, the capsule may comprise two optical windows from opposite sides.

When an in vivo procedure is being performed, in an area which includes many folds, e.g. the colon, the endoscope's imager may not be able to view a pathology placed within a fold. However, the capsule endoscope's imager, which views the fold from the opposite side, is able to view the pathology in the fold while the endoscope's medical tool, which can reach the pathology, is performing the procedure. Therefore, having both the capsule endoscope and endoscope imagers imaging from different sides of the body lumen where the procedure is being performed, increases the field of view of the procedure, in real-time.

Figure 4:
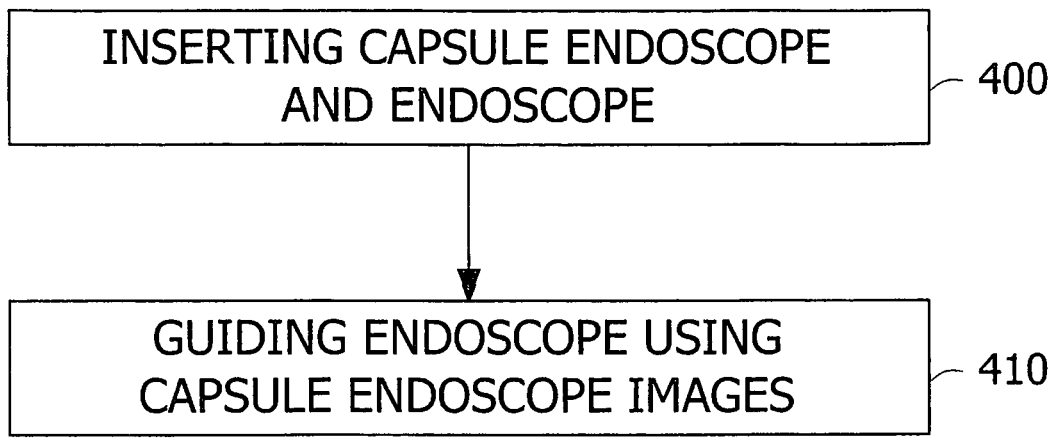
FIG. 4 depicts a method according to another embodiment of the present invention.

FIG. 4 depicts a method according to another embodiment of the present invention. Referring to FIG. 4, in step 400, a capsule endoscope and an endoscope assembly is inserted in vivo, into a body lumen. In some embodiments, the capsule endoscope may comprise two optical windows, each having at least one imager, at least one illumination source and an optical system behind them. In some embodiments, the capsule endoscope and the endoscope are attached through at least two semi rigid cables with a predetermined length. In some embodiments, the cables are positioned on the outer surface of the endoscope; however the cables may be positioned anywhere suitable. Any suitable number of cables or other attaching means may be used. In some embodiments of the present invention, the capsule endoscope may be partially wrapped about the outer surface of said endoscope when inserted into the body lumen with the endoscope. In step 410, the capsule endoscope is guiding the endoscope forward in the body lumen, while depending on the images of body lumen, obtained by an imager included inside the capsule. Typically, this step is done in real-time. In some embodiments, the position of the capsule in relation to the endoscope, when inserted as one assembly, may interfere with the endoscope's field of view, and therefore, images from the capsule first help guide the endoscope inside the lumen. In some embodiments, when the capsule and endoscope are inside the desired location in the body lumen, the capsule is then positioned in relation to the endoscope in a predetermined distance from it, according to the cables' length connecting both devices. According to some embodiments, an in vivo procedure can be performed, while both capsule and endoscope are viewing and/or imaging the body lumen site of the procedure, from different sides. In some embodiments, the capsule endoscope may comprise two optical windows from opposite sides of the capsule. In some embodiments, during step 410, a first capsule endoscope's imager positioned behind one optical window, obtains images of insertion into the body lumen and guidance of the endoscope. When a procedure is later performed, a second capsule endoscope's imager, placed behind the second optical window, typically positioned on an opposite side of the first imager, obtains images of the body lumen site of the procedure, while the endoscope obtains images of the opposite side of that lumen.

Figure 5:
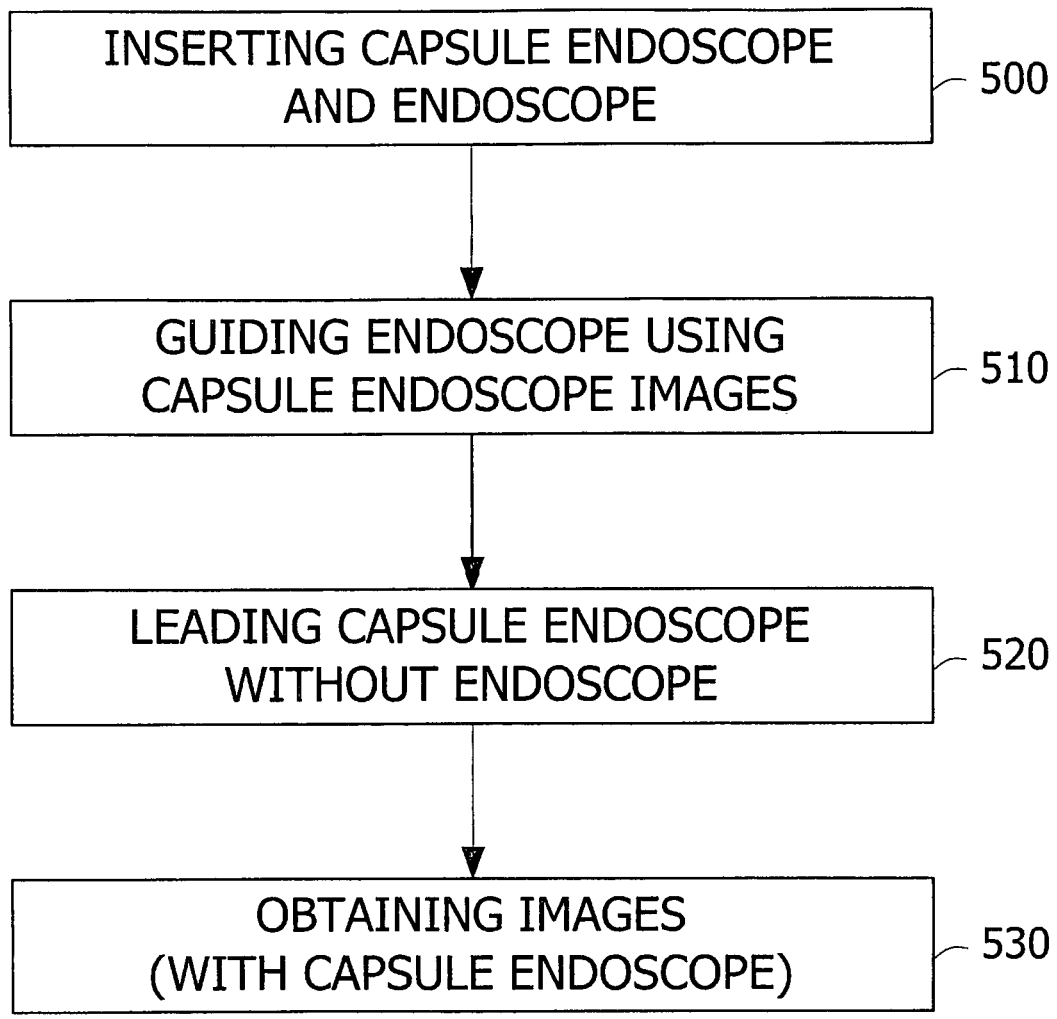
FIG. 5 depicts a method according to yet another embodiment of the present invention.

FIG. 5 depicts a method according to another embodiment of the present invention. Referring to FIG. 5, in step 500, a capsule endoscope and an endoscope assembly is inserted in vivo, into a body lumen. In some embodiments, the capsule endoscope and the endoscope are attached, for example, through at least two semi rigid cables. In step 510, the capsule endoscope is guiding the endoscope forward in the body lumen, while depending on the images of the body lumen, obtained by an imager included inside the capsule. Typically, this step is done in real-time. In some embodiments, the position of the capsule in relation to the endoscope interferes with the endoscope's field of view, and therefore, the capsule first guides the endoscope inside the lumen. In some cases, there might be difficulty in moving the endoscope forward without causing some damage to the lumen, for example, causing perforation. In step 520, the capsule is lead or passively moved inside the body lumen without the endoscope.

According to some embodiments, the capsule may still be connected to the endoscope and may be wired to the endoscope's external power supply. In other embodiments, the capsule may still be connected to the endoscope, and may not be connected to the endoscope's power supply. In some embodiments, the semi rigid cables connecting the capsule endoscope to the endoscope may be of a predetermined length. In some embodiments, the distance between the capsule endoscope and the endoscope may not be predetermined.

In step 530, the capsule endoscope is the only device obtaining images of the desired body lumen, since it is the only device which moved forward inside the body lumen. According to some embodiments, the capsule endoscope may be able to perform an in vivo procedure on its own, such as those an endoscope performs, e.g. stitching to close perforation, taking a biopsy, removing polyps, and other suitable procedures and treatment enabled by an endoscope. In some embodiments, the capsule endoscope may comprise sensors to sense the in vivo environment surrounding it, e.g. temperature sensors, pressure sensors, pH sensors, conductivity sensors, etc. In some embodiments, the endoscope may obtain images of the body lumen where it is last positioned, if required by the physician.

Figure 6:
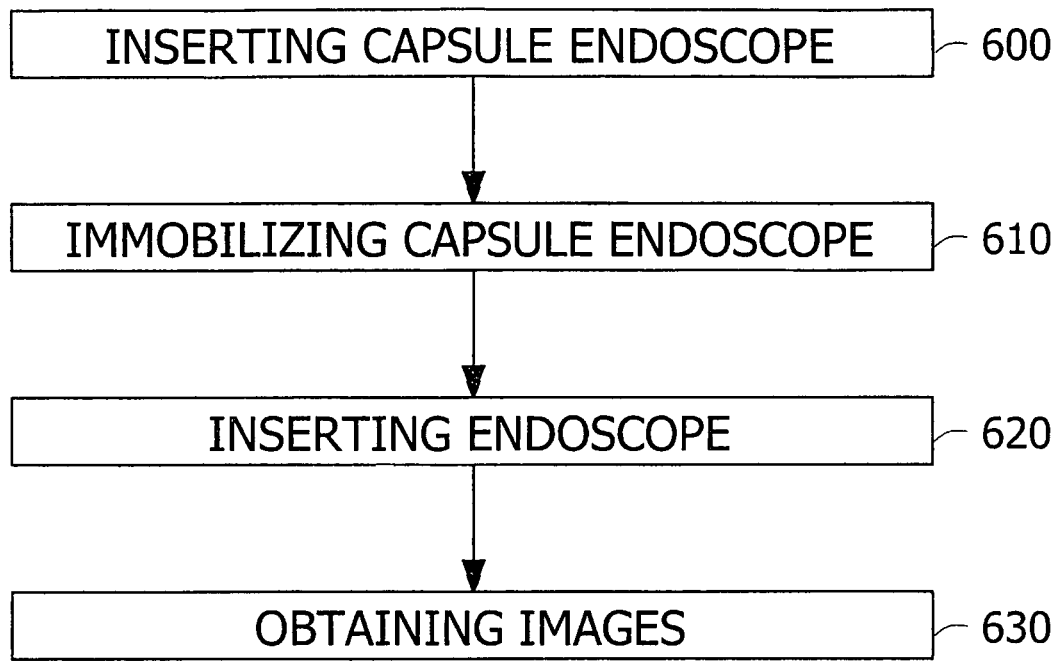
FIG. 6 depicts a method according to a further embodiment of the present invention.

FIG. 6 depicts a method according to another embodiment of the present invention. Referring to FIG. 6, in step 600, a capsule endoscope is inserted in vivo, into a body lumen. In some embodiments, the capsule may be swallowed by the patient. In some embodiments the capsule may passively progress through the body lumen, pushed along by natural peristalsis. In some embodiments the capsule may be actively progressed through the body lumen. In step 610, the capsule is immobilized to the body lumen at a desired location. In some embodiments, the immobilization of the capsule may be done through pins, clasps, fasteners and suction means. In some embodiments the immobilization may be controlled by an external transmitter sending commands to the capsule, which contains a receiver (e.g., an RF receiver) within. In step 620, the endoscope is inserted in vivo, into the body lumen, to a desired location, for example, to the location the capsule is immobilized at. According to some embodiments, a physician would be able to easily decide through which side to insert the endoscope, either the mouth or the anus, based on the location of the capsule endoscope inside the body. If the capsule is closer to the mouth, this may be the side through which the endoscope would be inserted from. If the capsule is closer, for example, to the colon then the endoscope would probably be inserted through the anus. In step 630, both the capsule endoscope and the endoscope are obtaining images of the desired location in the body lumen. In some embodiments the capsule and endoscope are obtaining images from opposite sides of the location. Other viewing angles may be used. In some embodiments the capsule may comprise two optical windows positioned on opposite sides of the capsule.

It will be appreciated that the present invention is not limited to what has been particularly shown and described hereinabove. Rather the scope of the present invention is defined only by the claims which follow.

What is claimed is:

1. An in-vivo imaging device comprising:
   a non-cylindrical housing having a concave cross-section with a first surface having a concave shape opposing a second surface having a convex shape, said housing comprising between said first and second surfaces:
   an optical window;
   at least one imager;
   at least one illumination source; and
   an optical system,
   wherein said concave shaped surface of said housing is adapted to attach to, and partially wrap around, a correspondingly curved external surface of an endoscope, the endoscope having an insertion direction corresponding to a direction at which the endoscope is inserted into a body lumen;
   wherein the at least one of said at least one imager is configured to image in a direction opposite to the endoscope insertion direction, and
   wherein said housing is configured to attach to, and detach from, the external surface of the endoscope via said concave shaped surface of said housing using an attachment means;
   wherein, following insertion of the in-vivo imaging device and the endoscope to a first side of a desired location within the body lumen, said in-vivo imaging device is adapted to move, via said attachment means, a predetermined distance from the endoscope, from a position in which said housing is attached to the endoscope at the first side of the desired location to a position in which said housing is detached from the endoscope at a second side of the desired location opposing the first side, such that said at least one of said at least one imager is configured to image the desired location from the second side of the desired location opposing the first side, in the direction opposite to the endoscope insertion direction.

2. The in-vivo imaging device of claim 1, wherein said at least one imager, said at least one illumination source, and said optical system are positioned behind said optical window.

3. The in-vivo imaging device of claim 1, wherein said attachment means comprises at least two semi rigid cables with a predetermined length.

4. The in-vivo imaging device of claim 1, further comprising a transmitter.

5. The in-vivo imaging device of claim 4, wherein said transmitter is a wireless transmitter.

6. The in-vivo imaging device of claim 1, wherein said in-vivo imaging device is configured to be powered through an electrical wire connected to said endoscope.

7. The in-vivo imaging device of claim 1, wherein said endoscope comprises an imager, and wherein said endoscope imager and at least one of said at least one imager of the in-vivo imaging device are configured to obtain images from the first and second sides of said desired location, respectively.

8. A method for viewing a body lumen, the method comprising:
   inserting an in-vivo imaging device and an endoscope in a first direction into a body lumen, wherein said in-vivo imaging device comprises a non-cylindrical housing having a concave cross-section with a first surface having a concave shape opposing a second surface having a convex shape, said housing comprising between said first and second surfaces an optical window, at least one imager, at least one illumination source, and an optical system, wherein said concave shaped surface is configured to attach to and partially wrap around a correspondingly curved external surface of said endoscope, wherein said housing is configured to attach to, and detach from, the external surface of the endoscope via said concave shaped surface of said housing using an attachment means;

positioning the endoscope and said attached in-vivo imaging device at a first side of a desired location within the body lumen;

moving said in-vivo imaging device, via said attachment means, a predetermined distance from said endoscope, from a position in which said in-vivo imaging device is attached to the endoscope at the first side of the desired location to a position in which said in-vivo imaging device is detached from the endoscope at a second side of the desired location opposing the first side; and obtaining images of the desired location from the second side of the desired location opposing the first side in the direction opposite to said first direction using said in-vivo imaging device.

9. The method of claim 8, wherein said endoscope comprises an imager, the method further comprising performing an in-vivo procedure at said desired location while obtaining images from both the first and the second sides of the desired location.

10. The method according to claim 8, wherein said at least one imager, said at least one illumination source and said optical system are positioned behind said optical window.

11. The method according to claim 8, wherein said in-vivo imaging device comprises two optical windows.

12. The method according to claim 8, wherein said attachment means comprises at least two semi rigid cables with a predetermined length.

13. The method of claim 8, said method further comprising receiving control signals at said in-vivo imaging device from an external transceiver.

14. The method according claim 8, further comprising transmitting the images to a receiver external to the in-vivo imaging device.

15. The method according claim 8, further comprising powering the in-vivo imaging device through an electrical wire connected to the endoscope.

16. A method for viewing a body lumen, the method comprising:

inserting an in-vivo imaging device and an endoscope in a first direction into a body lumen, wherein said in-vivo imaging device comprises a non-cylindrical housing having a concave cross-section with a first surface having a concave shape opposing a second surface having a convex shape, said housing comprising between said first and second surfaces an optical window, at least one imager, at least one illumination source, and an optical system, said concaved shaped surface configured to attach to and partially wrap around a correspondingly curved external surface of said endoscope, wherein said housing is configured to attach to, and detach from, the external surface of the endoscope via said concave shaped surface of said housing using an attachment means;

guiding the endoscope and said attached in-vivo imaging device to a first side of a desired location in the body lumen using images obtained from said first direction by said in-vivo imaging device;

moving said in-vivo imaging device, via said attachment means, a predetermined distance from said endoscope, from a position in which said in-vivo imaging device is attached to the endoscope at the first side of the desired location to a position in which said in-vivo imaging device is detached from the endoscope at a second side of the desired location opposing the first side; and obtaining images of the desired location from the second side of the desired location opposing the first side in the direction opposite to said first direction using said in-vivo imaging device.

17. The method according to claim 16, wherein said endoscope comprises an imager, said method further comprising performing an in-vivo procedure at said desired location while obtaining images from both the first and the second sides of said location.

18. The method according to claim 16, wherein said in-vivo imaging device comprises two optical windows.

19. The method according claim 16, further comprising transmitting the images to a receiver external to the in-vivo imaging device.

20. The method according claim 16, further comprising powering the in-vivo imaging device through an electrical wire connected to the endoscope.

21. A method for viewing a body lumen, the method comprising:

inserting an in-vivo imaging device and an endoscope in a first direction into a body lumen, wherein said in-vivo imaging device comprises a non-cylindrical housing having a concave cross-section with a first surface having a concave shape opposing a second surface having a convex shape, said housing comprising between said first and second surfaces an optical window, at least one imager, at least one illumination source, and an optical system, said concave shaped portion configured to attach to and partially wrap around a correspondingly curved external surface of said endoscope, wherein said housing is configured to attach to, and detach from, the external surface of the endoscope via said concave shaped surface of said housing using an attachment means;

guiding the endoscope and said attached in-vivo imaging device to a first side of a desired location in the body lumen using images obtained by said in-vivo imaging device until no further movement is possible;

leading said in-vivo imaging device, via said attachment means, a predetermined distance further in the body lumen, without the endoscope, while said in-vivo imaging device remains attached to said endoscope via said attachment means; and obtaining images of the desired location using said in-vivo imaging device from a second side of the desired location opposing the first side in the direction opposite to said first direction.

22. The method of claim 21, wherein said endoscope comprises an imager, the method further comprising performing an in-vivo procedure at said desired location while obtaining images from both the first and the second sides of said location.

23. The method according claim 21, further comprising powering the in-vivo imaging device through an electrical wire connected to the endoscope.

* * * * *